Figure 1:
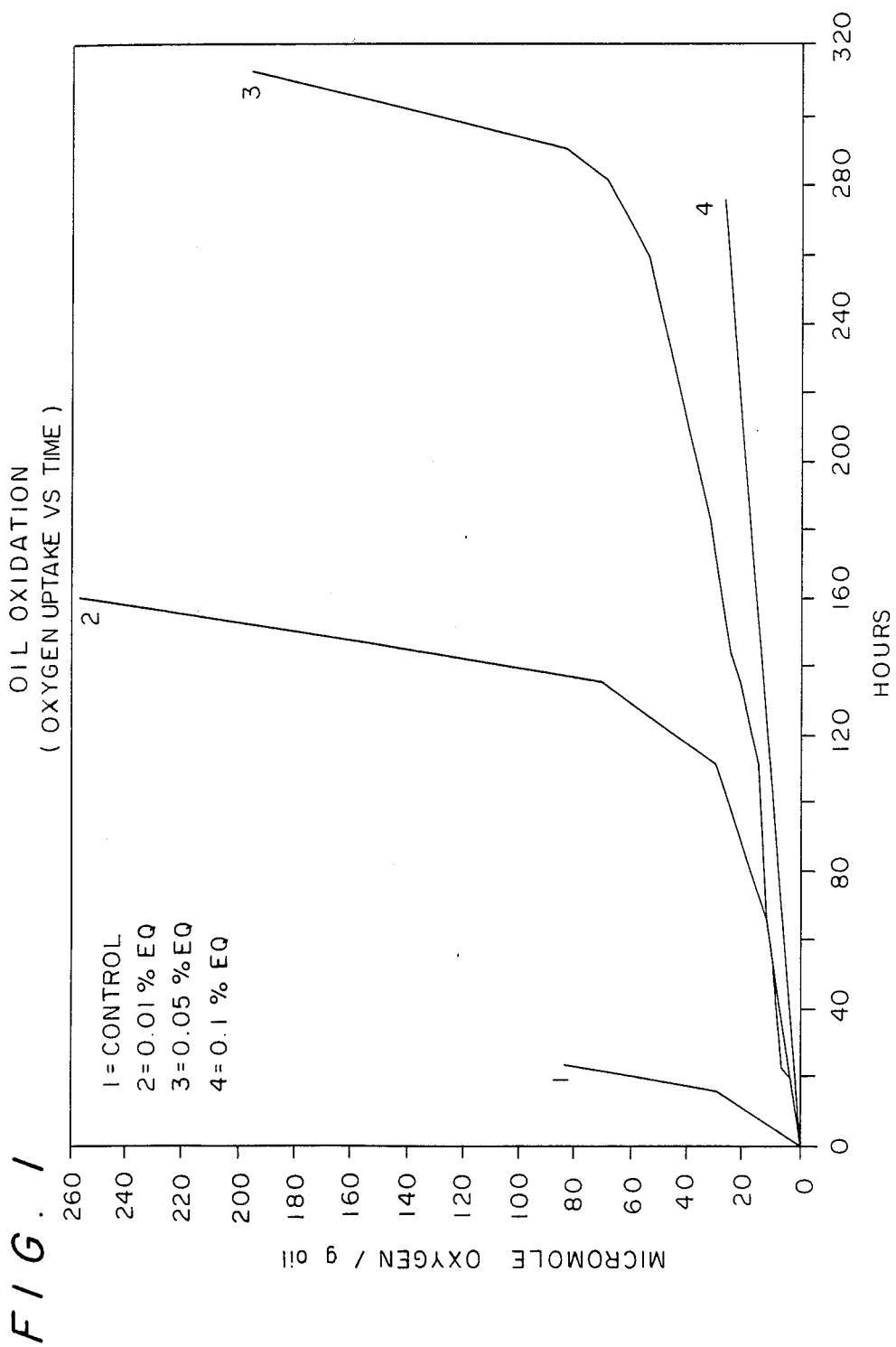

United States Patent [19]

Barlow et al.

[11] Patent Number: 4,986,996

[45] Date of Patent: Jan. 22, 1991

[54] ETHOXYQUIN DERIVATIVES AS ANTIOXIDANTS IN EDIBLE OILS AND FISH MEAL

[75] Inventors: Stuart M. Barlow, Hoddesdon, Great Britain; Frank D. Gunstone, Cupar; Roy Hardy, Aberdeen, both of Scotland; Snorri Thorisson, Reykjavik, Iceland

[73] Assignee: University of St. Andrews, Scotland

[21] Appl. No.: 376,285

[22] Filed: Jul. 6, 1989

[30] Foreign Application Priority Data

Jul. 8, 1988 [GB] United Kingdom ............... 8816269

[51] Int. Cl.$^5$ .................... A23B 4/14; A23D 5/04; A23K 3/00

[52] U.S. Cl. .................. 426/545; 426/544; 260/398.5; 546/153

[58] Field of Search ............. 426/545, 544, 541, 102, 426/286, 273, 252, 419; 260/398.5; 546/153

[56] References Cited

U.S. PATENT DOCUMENTS

| | | | |
|---|---|---|---|
| 1,585,371 | 5/1926 | Brogden | 426/102 |
| 2,562,970 | 8/1967 | Thompson | 426/545 |
| 2,633,425 | 3/1953 | Thompson | 260/398.5 |
| 2,648,608 | 8/1953 | Beadle | 426/541 |
| 2,886,568 | 5/1959 | Stansbury | 546/153 |
| 2,948,680 | 8/1960 | Fields | 426/545 |
| 3,024,217 | 3/1962 | Kibler | 546/153 |
| 3,075,984 | 1/1963 | Surrey | 546/153 |
| 3,149,117 | 9/1964 | Brown | 546/153 |
| 3,178,348 | 4/1965 | Buckerton | 546/153 |
| 3,252,853 | 5/1966 | Goodhue | 546/153 |
| 3,262,906 | 7/1966 | Perry | 546/153 |
| 3,278,308 | 10/1966 | Marco | 426/545 |
| 3,325,288 | 6/1967 | Tung | 426/545 |
| 3,347,677 | 10/1967 | Jaworski | 426/545 |
| 3,637,844 | 1/1972 | Trivette | 546/153 |
| 4,079,153 | 3/1978 | Coleman | 426/545 |
| 4,363,910 | 12/1982 | Ambrus | 426/545 |

OTHER PUBLICATIONS

Chahine 1978 Chemical Abstracts 89(5)40998a.

*Primary Examiner*—Carolyn Paden
*Attorney, Agent, or Firm*—Foley & Lardner, Schwartz, Jeffery, Schwaab, Mack, Blumenthal & Evans

[57] ABSTRACT

Anti-oxidants for natural and processed oils, including fish oil and fish meal and animal feed, are 8-substituted ethoxyquin derivatives which, unlike ethoxyquin, do not dimerize on oxidation. Many of the derivatives are novel compounds.

15 Claims, 3 Drawing Sheets

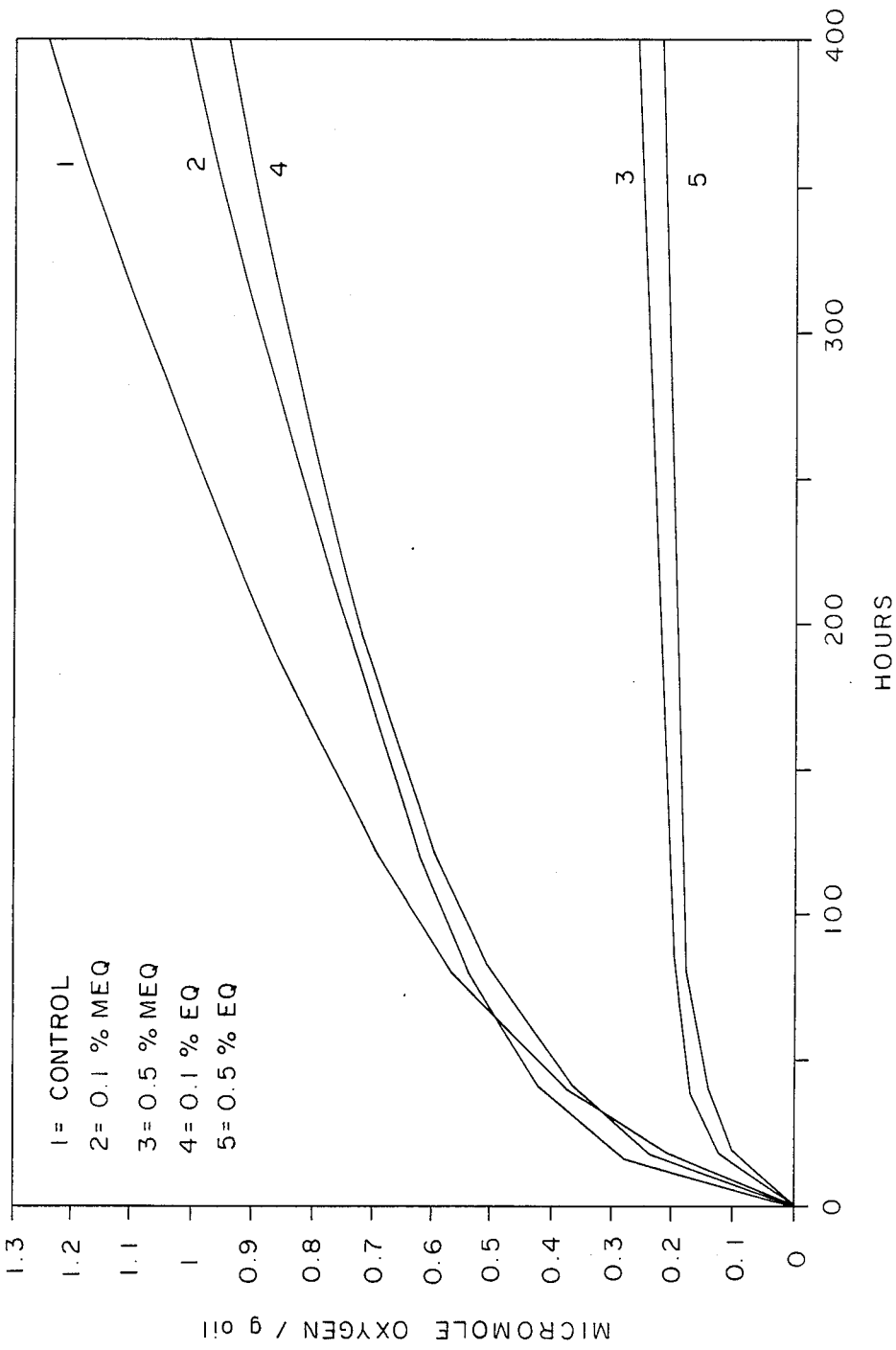

ETHOXYQUIN DERIVATIVES AS ANTIOXIDANTS IN EDIBLE OILS AND FISH MEAL

FIELD OF THE INVENTION

This invention relates to compounds for use as anti-oxidants in oils.

BACKGROUND OF THE INVENTION

Fish meal is a product obtained by drying and grinding fish or fish waste to which no other matter has been added. The fish or fish waste is usually cooked, the oil and water removed by pressing, and the solids dried to approximately 10% water content. The oil content can vary from 5 to 20%, depending on the raw material and the processing.

Owing to the high unsaturation of fish oil, fish meal is readily autoxidised, with a consequent decrease in nutritional and energy values. Lipid autoxidation in fish meal also causes heat-production which can even lead to spontaneous combustion of stored meal. If a low quality raw material is used, oxidation is likely to be faster.

The risk of spontaneous heating in fish meal can be decreased by "curing", i.e. heating the meal and allowing the autoxidation to proceed before storing or transport. However, if the nutritional or energy levels are to be maintained, anti-oxidants must be used.

Ethoxyquin has been widely approved for us in animal feed and is the most commonly used anti-oxidant in fish meal intended for that use. Despite its widespread use as an anti-oxidant in fish meal, the mode of action of ethoxyquin is unclear. For example, while the effect of adding the compound to fish meal may be observed for a period of say, two years, analysis of the composition fails to detect the presence of ethoxyquin per se within a matter of hours.

Ethoxyquin is a compound of formula I (see below) in which $R=Et$, $X=H$. Its preparation and its use as a rubber anti-oxidant, are described in GB-A-No. 0505113. Compounds of formula I ($R=C_{1-5}$alkyl and $X=H$), including ethoxyquin, and their use as herbicides, are described in U.S. Pat. No. 2661277.

Bharucha et al, J. Agric. Food Chem. 33(5) (1985) 834-9, disclose that ethoxyquin is a potent inhibitor of nitrosamine formation in bacon, and also that 8-nitrosoethoxyquin (I:$R=Et$, $X=NO$) and 8-nitroethoxyquin (I:$R=Et$, $X=NO_2$) are apparently formed in situ.

Other known 8-substituted ethoxyquin analogues are 2,2,4,8-tetramethyl-6-methoxy-1,2-dihydroquinoline (I:$R=X=Me$) and 8-hydroxyethoxyquin (I:$R=Et$, $X=OH$). The former is disclosed as a pressure-sensitive dye precursor in Chem. Abs. 95 (1981) 99338n, and the latter as a metabolite of ethoxyquin, in the rat, by Skaare, Xenobiotica 9(11) (1979) 659–668.

SUMMARY OF THE INVENTION

It has been discovered that ethoxyquin is converted to two main oxidation products: a 1,8'-dimer (formula II) having no anti-oxidant properties and 2,6-dihydro-2,2,4-trimethyl-6-quinolone (III:$X=H$).

With the object of controlling the behaviour of an effective anti-oxidant for animal feedstuffs and natural and refined or other wise processed oils, including vegetable oil, fish meal and fish oil, compounds hereinafter described as "ethoxyquin derivatives" have been prepared. The derivatives, many of which are novel, are of formula I, in Which R is $C_{1-5}$ alkyl and X is not hydrogen but a substituent which does not substantially decrease the anti-oxidant effect of the compound below that of ethoxyquin but prevents dimerisation of the molecule. In consequence, the sole or major product of oxidation can be the corresponding compound of formula III.

DESCRIPTION OF THE INVENTION

The derivatives for use in the invention are 8-substituted ethoxyquin analogues. R will usually be ethyl, as in ethoxyquin. X may be a straight or branched-chain alkyl group, such as methyl; aryl, e.g. $C_{6-12}$aryl; dialkylamino; alkylthio; alkoxy; OH; or halogen, e.g. Cl. Any alkyl group may have up to 5 or 8 C atoms, or more. Examples of X as aryl are 4-aminophenyl, 3,4-dihydroxyphenyl (optionally alkylated, e.g. by methyl or t-butyl, in the 2 or 5 position), or 2,5-hydroxyphenyl (optionally substituted, e.g. by methyl or t-butyl in the 3,4 or 6 positions).

Novel compounds of the invention are those of formula I as defined above, except those in which $R=Et$, $X=NO$; $R=Et$, $X=NO_2$; $R=Et$, $X=OH$; $R=Me$, $X=Me$.

An ethoxyquin derivative of formula I may be incorporated in animal feed, fish meal, fish oil or other natural or processed oil in a conventional amount, such as 0.001 to 1, preferably 0.01 to 0.1, % by weight, e.g. 700–1000 mg/kg fish meal. The ethoxyquin derivative may be added to a carrier such as fish oil, fish meal or intended for incorporation into an animal feed containing natural or processed oil.

Ethoxyquin derivatives of formula I may be less effective anti-oxidants per se than ethoxyquin, but are probably more reliable. This is because the main oxidation product of ethoxyquin is a dimer which is an ineffective anti-oxidant, and may indeed constitute a health hazard. The yield of the dimer probably increases with increased oxidation level of the meal. Depending on the nature of X, however, compounds of the invention may be not only more reliable than ethoxyquin, but also anti-oxidants which are at least as effective.

When an ethoxyquin derivative of formula I is oxidised, e.g. with tert-butylhydroperoxide in the presence of ferrous iron, the corresponding quinolone of formula III is obtained. For example, when X is methyl, no dimer was prepared.

Ethoxyquin derivatives for use in the invention may be prepared by reacting a compound of formula IV with acetone and an oxidising agent such as iodine. Their synthesis is illustrated below:

EXAMPLE 1

8-Methylethoxyquin (i) Potassium 3-methyl-4-nitrophenoxide.

A solution of 3-methyl-4-nitrophenol (35 g) in ethanolic potassium hydroxide (100 ml, 2.5 M) was refluxed for 30 min. The solvent was then removed on a rotary evaporator and the remaining solid was washed with diethyl ether (3 ×250 ml), leaving the potassium salt (2) as a yellow solid (96%, m p. about 300° C. with 5 decomposition).

(ii) 4-Ethoxy-2-methylnitrobenzene.

The potassium phenate (35 g) was heated at 150° C. for 24 hours with ethanol (44 ml) and ethyl bromide (25 g) in a closed pressure vessel. The product was transferred to a flask and the reaction vessel washed out with ether. Volatile solvents were removed on a rotary evaporator and the product, mixed with aqueous sodium hydroxide (500 ml, 0.1 M), was extracted with diethyl ether (2×500 ml and 2×250 ml). The combined ether extracts were washed with water (2×100 ml) and filtered. Solvent was then removed on a rotary evaporator and water was finally removed by azeotropic distillation with acetone, yielding the title compound as a brown solid (83%, m.p. 50°–51° C.).

(iii) 4-Ethoxy-2-methylaniline.

The crude nitro compound (25 g) was hydrogenated in ethanol solution (200 ml) using Raney nickel as catalyst (10 g as supplied by Aldrich). When no further hydrogen was absorbed, the solution was decanted from the nickel and the solvent was removed on a rotary evaporator. The residue was dissolved in ether (200 ml) and extracted with aqueous hydrochloric acid (1 M, 3×100 ml). The combined acid extracts were washed with ether (100 ml) then made alkaline with aqueous sodium hydroxide (5 M). The amine was extracted with ether (3×200 ml) and the ether solutions were washed with water (2×100 ml). Removal of solvent on the rotary evaporator left an oil (19.7 g, 95%) which was purified by column chromatography (silica, eluted with petroleum ether (b.p. 40–60) containing increasing proportions of ether). The crude product contained some unreacted nitro compound and also some N-ethyl-4-ethoxy-2-methylquinoline (3%). The title compound appeared as a blue spot after spraying the tlc plate (PE20) with phosphomolybdic acid ($R_f$ 0.16). The N-ethyl derivative appeared similarly as a blue spot ($R_f$7 15 0.57).

(iv) 1,2-Dihydro-6-ethoxy-2,2,4,8-tetramethylquinoline.

The amine (2.6 g), acetone (4.0 g), and iodine (59 mg) were placed in a pressure vessel which was flushed with nitrogen before heating to 170° C. for 48 hr. The reaction mixture, dissolved in diethyl ether (100 ml), was extracted with aqueous hydrochloric acid (0.1 M, 2×100 ml, 1.0 M, 2×100 ml). The first two extracts with dilute acid contained mainly unreacted amine (1.37 g). The last two extracts with stronger acid were washed with ether (50 ml), made basic with aqueous sodium hydroxide (5.0 M), and extracted with ether (2×100 ml). After washing with water and evaporation of solvent a dark oil (0.99 g) remained. This was purified by passage through a column of silica (20×2 cm) being eluted with petroleum ether (b.p. 40°–50° C.) containing increasing proportions of diethyl ether. The dihydroquinoline compound was a yellow oil (0.56 g, 14%) which solidified (m.p. 42°–43° C.) when cooled.

EXAMPLE 2

8-Ethoxyethoxyquin 2,4-D:ethoxyaniline (24 g), acetone (about 50 g), and 4-toluenesulphonic acid (about 100 mg) were heated together at 180° C. in a sealed vessel for 24 hours. Thereafter the mixture was concentrated under reduced pressure and the residue was chromatographed on a column of silica gel (1bout 150 g). Elution with diethyl ether and cyclohexane (1:9) afforded crude product as a red solid. Short-path distillation (Kugelrohr) gave 8-ethoxyethoxyquin (8.40 g, 24%, b.p. about 220° C./2 mm Hg) as a pale orange solid.

Oxidation

8-Methylethoxyquin (50 mg in 5 ml ethanol), an equimolar amount of tert-butylhydroperoxide (20 mg), and an aqueous solution of ferrous ammonium sulphate (1 ml containing 43 mg) were mixed and stirred in the dark for 24 hours. Water was then added (25 ml) and the product extracted with ether (25 ml). For comparison purposes, a sample of ethoxyquin was treated in the same way. The reaction product was separated into its components by preparative tlc (PE20) and the components identified spectroscopically.

The major oxidation product of 8-methylethoxyquin was a yellow compound ($R_f$ 0.37 PE 20) formed in about 60% yield and identified as the quinoline (III: X=CH$_3$). No dimer was identified.

Antioxidant Properties

The following experiments were carried out to compare the anti-oxidant properties of ethoxyquin and methylethoxyquin in respect of methyl linoleate, fish oil and fish meal (oxygen uptake was measured by the Warburg manometric technique at 30° C.): the anti-oxidant was dissolved in hexane and an appropriate volume, to provide 0.01, 0.05 or 0.1% concentration, was placed in a graduated flask (25 ml). The solvent was removed under a stream of nitrogen, and fish oil (5.0 g) was added and mixed thoroughly. To allow for thermal equilibrium, the flasks were left open for one hour in the water bath before readings were started. To secure high enough partial pressure of oxygen, air exchange with a vacuum pump was effected after each reading. The comparative results are given in FIGS. 1 and 2.

For the fish meal studies, the anti-oxidant solution was pipetted on to the meal (50 g) which was then shaken with hexane (200 ml) for 1 min. The solvent was removed on a rotary evaporator until the sample reached its original weight. Duplicate samples (20 g) of meal with 0.1 and 0.5% anti-oxidant (on an oil basis) were oxidised at 30° C in calibrated flasks (100 ml). The results are shown in FIG. 3.

For the methyl linoleate oxidation, anti-oxidant was placed in the flask as before followed by methyl linoleate (0.25 g) and a solution of azoisobutyronitrile (AIBN) in chlorobenzene (1 ml, 5.8×10$^{-2}$M). The final linoleate concentration was 6.8 ×10$^{-1}$ M and anti-oxidant concentrations were between 1 and 10 ×10−4 flasks were placed in a water bath at 50° C., kept open for 10 min, and oxygen uptake then measured. The inhibition period was determined and the stoichiometric factor (n) calculated using BHT (n=2) as a control.

Figure 2:
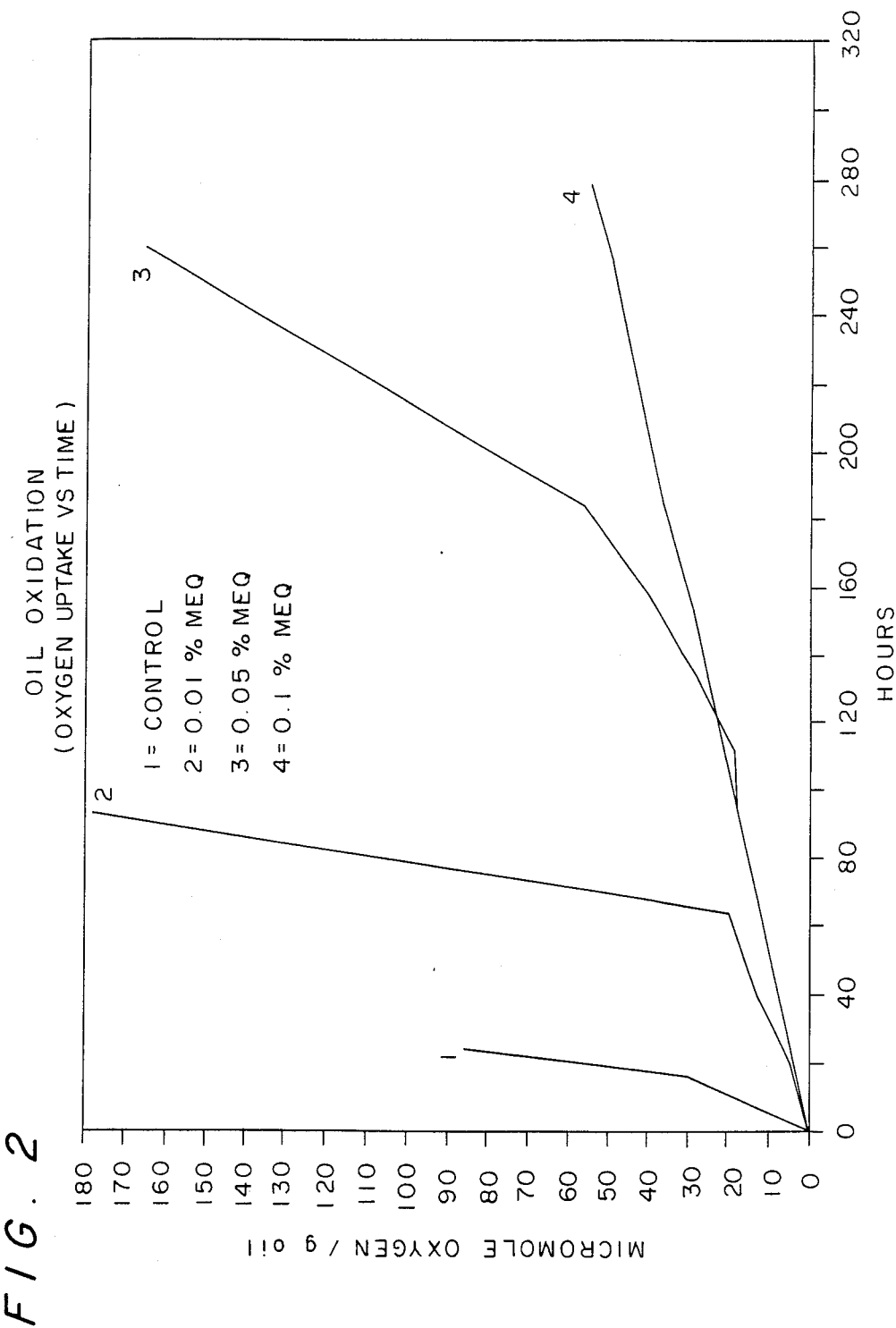

The results set out in FIGS. 1 and 2 show that ethoxyquin is a more effective anti-oxidant that its 8-methyl derivative in fish oil at each of the three concentrations examined (0.01, 0.05 and 0.1%). A similar result was obtained with fish meal, although the difference between the two anti-oxidants was much less marked than in the oil (FIG. 3).

From the AIBN-initiated oxidation of methyl linoleate, it is possible to determine the number of autoxidation chains stopped by each molecule inhibitor. These were 2.5 and 3.0 for ethoxyquin and its 8-methyl derivative, respectively.

Without wishing to be bound by theory, it is suggested that, despite the fact that 8-methylethoxyquin gives more quinolone than ethoxyquin under oxidative conditions, the quinolone derived from the latter (III:R-=Et, X=H) is a more effective anti-oxidant than the quinolone derived from the former (III: R=Et, X=Me).

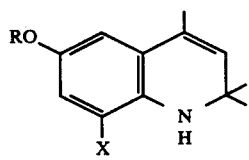

I

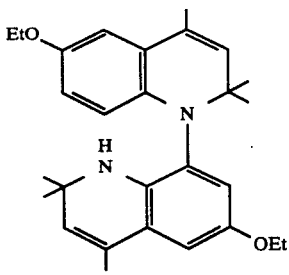

II

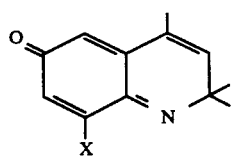

III

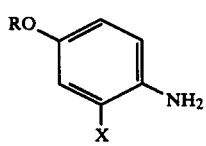

IV

What is claimed is:

1. A composition comprising a natural or processed oil and an anti-oxidant amount of a compound of the formula

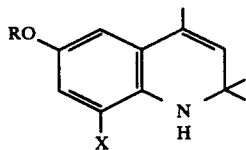

I wherein R is $C_{1-5}$ alkyl and X is not hydrogen but a substituent which prevents dimerisation of the compound on oxidation but does not substantially decrease the anti-oxidant effect of the compound below that when X is H.

2. A composition according to claim 1, in which X is alkyl, aryl, dialkylamino, alkylthio, alkoxy, OH or halogen.

3. A composition according to claim 1, in which said compound is 6-ethoxy-2,2,4,8-tetramethyl-1,2-dihydroquinoline.

4. A composition according to claim 1, in which said compound is 6,8-diethoxy-2,2,4-trimethyl-1,2-dihydroquinoline.

5. A composition according to claim 1, which comprises 0.01 to 0.1% by weight of the compound.

6. A composition comprising fish meal or fish oil and an anti-oxidant effective amount of a compound of the formula

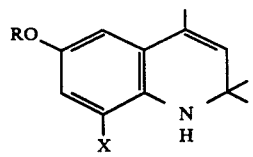

I wherein R is $C_{1-5}$ alkyl and X is not hydrogen but a substituent which prevents dimerisation of the compound on oxidation but does not substantially decrease the anti-oxidant effect of the compound below that when X is H.

7. A composition according to claim 6, in which X is alkyl, aryl, dialkylamino, alkylthio, alkoxy, OH or halogen.

8. A composition according to claim 6, in which said compound is 6-ethoxy-2,2,4,8-tetramethyl-1,2-dihydroquinoline.

9. A composition according to claim 6, in which said compound is 6,8-diethoxy-2,2,4-trimethyl-1,2-dihydroquinoline.

10. A composition according to claim 6, which comprises 0.01 to 0.1% by weight of the compound.

11. An animal feed composition comprising an anti-oxidant effective amount of a compound of the formula

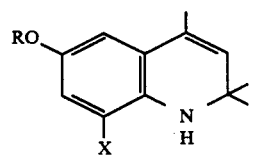

I wherein R is $C_{1-5}$ alkyl and X is not hydrogen but a substituent which prevents dimerisation of the compound on oxidation but does not substantially decrease the anti-oxidation but does not substantially decrease the anti-oxidant effect of the compound below that when X is H.

12. A composition according to claim 11, in which X is alkyl, aryl, dialkylamino, alkylthio, alkoxy, OH or halogen.

13. A composition according to claim 11, in which said compound is 6-ethoxy-2,2,4,8-tetramethyl-1,2-dihydroquinoline.

14. A composition according to claim 11, in which said compound is 6,8-diethoxy-2,2,4-trimethyl-1,2-dihydroquinoline.

15. A composition according to claim 11, which comprises 0.01 to 0.1% by weight of the compound.

* * * * *